United States Patent [19]

Downey et al.

[11] 4,358,338
[45] Nov. 9, 1982

[54] END POINT DETECTION METHOD FOR PHYSICAL ETCHING PROCESS

[75] Inventors: Daniel F. Downey, Magnolia; George T. Lecouras, Lynn, both of Mass.

[73] Assignee: Varian Associates, Inc., Palo Alto, Calif.

[21] Appl. No.: 150,533

[22] Filed: May 16, 1980

[51] Int. Cl.³ .................. H01L 21/306; C23F 1/00
[52] U.S. Cl. ........................... 156/627; 156/643; 204/192 E; 324/71 E
[58] Field of Search .............. 204/192 E, 298; 324/62, 324/71 E; 156/626, 627, 643, 646, 653, 657, 662, 345

[56] References Cited

FOREIGN PATENT DOCUMENTS 52-58476  5/1977  Japan ................................ 156/643

OTHER PUBLICATIONS

Production and Manipulation of Ion Beams [4 and 5], Target Chambers, Ion Beam Current Measurements, Ion Implantation by G. Dearnaley et al., 1973, pp. 416-421.
European Conference on Ion Implantation, Sep. 7-9, 1970, by J. H. Freeman, pp. 1-18.

Primary Examiner—William A. Powell
Attorney, Agent, or Firm—Stanley Z. Cole; Norman E. Reitz

[57] ABSTRACT

A method for determining the end point for a physical etching process step measures the current at the target being etched and detects changes in the current. Changes in the current measured at the target are indicative of transitions between dissimilar materials or of depth of penetration in a particular material. Momentary changes in the etching flux of the physical etching process are factored out by measuring the current on a mask placed in the vicinity of the target and by subtracting mask current from current measured at the target.

7 Claims, 10 Drawing Figures

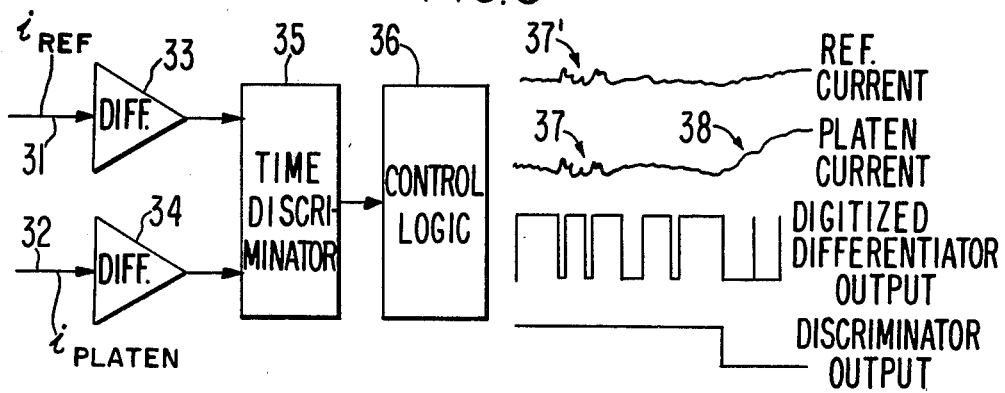
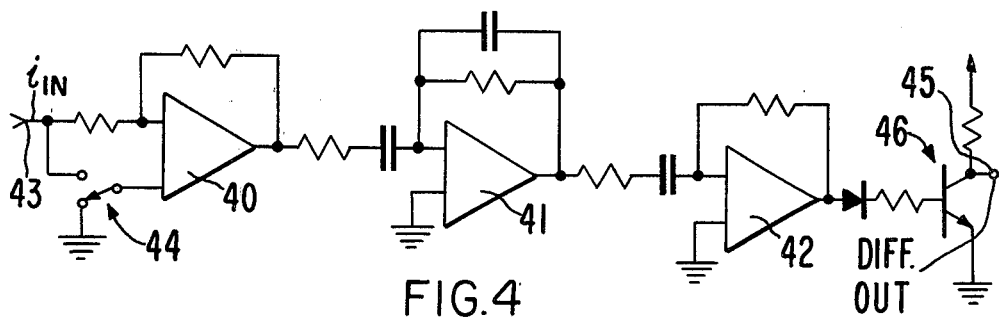
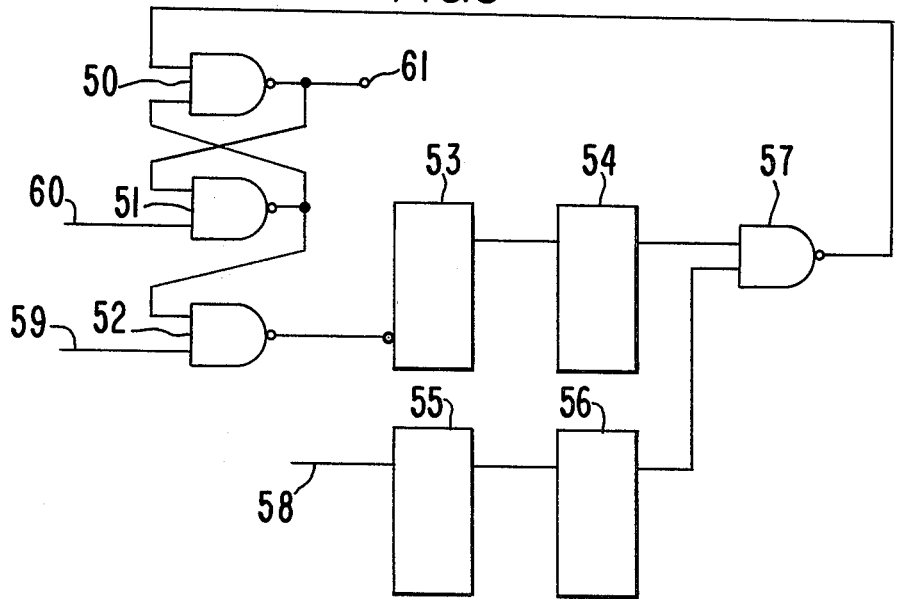

END POINT DETECTION METHOD FOR PHYSICAL ETCHING PROCESS

DESCRIPTION

This invention relates to a method for determining the end point for a physical etching process step and, more particularly, relates to a method which monitors current through the target to determine when a physical etching process step reaches an end point.

The field of selective removal of materials to define a pattern on a surface has typically involved abrading by hard workpieces with or without abrasives or etching by wet chemical processes. In the semiconductor industry where photoresist, insulators, conductive layers, or semiconductor material are patterned in the fabrication of integrated circuits it has not been possible to use abrasives because of the fine geometries involved and because the abrasive residue would contaminate the circuits being produced. While wet chemical etching has been used in the semiconductor industry it has become increasingly undesirable to use such etching due to the expense, time, handling requirements and the need to dispose of toxic waste chemicals.

In view of the background given above, there has been a trend towards physical etching which uses plasma constituents to selectively remove substrate material. With ion milling and reactive ion etch energetic ion beams which have either been accelerated towards the target or created in a sputter discharge with sufficient momentum are used. This is essentially an atomic or molecular sandblasting which allows very fine patterns to be obtained and leaves little residue. It is advantageous because the residue is easily carried away and no toxic wastes are generated. In ion milling the kinetic energy of nonreactive atomic or molecular species are relied upon to produce etching. With reactive ion etch reactive molecules have been utilized to combine these kinetic effects with chemical effects to enhance etching rates and to produce selectivity.

As semiconductor processing progresses to the fabrication of increasingly more complex structures, it has become increasingly desirable to develop more effective etching techniques and to obtain higher throughput. In particular, it is desirable to avoid undercutting and to avoid overetching. With LSI structures it is desirable to etch with a fine control over the depth of etch, i.e., one does not want to do damage to underlying layers. Therefore, it is highly desirable to be able to determine how far one has gone in a given material and to determine when one reaches an interface between dissimilar materials. This information has previously been obtained by measuring ion beam intensity and exposure time. However, with higher beam intensities which must be used to obtain high throughput it is possible to overshoot boundaries in short time periods and damage critical regions of the integrated circuits being fabricated. Thus, it is especially desirable to have an instantaneous indication of the etching of an ion beam through a boundary between dissimilar materials, e.g., the boundary between a conductor and an insulator or an insulator and a semiconductor substrate.

In existing ion etching systems several different end point detection techniques have been used. Quartz crystal microbalances have been used to weigh the specimen while it is being etched. As the specimen is etched it loses weight, and by knowing the area being etched and the density of the material, one can determine the depth of etch. Another approach utilizes quadrapole gas analyzers to detect the presence of particular gaseous species in the system. Thus, when a certain species is detected, it would be known that a boundary between dissimilar materials has been reached. This approach is capable of determining whether a particular layer has been reached but it is not especially suitable for depth of etch measurements. The prevalent technique is controlling length of etch with reference to calibrated etching rates. This approach is useful if one utilizes selective etchants, i.e., etchants that etch the overlying material in question at a much higher rate than the underlying material. Use of controlled time etches with selective etchants is satisfactory if you have a selective etchant with etch ratios on the order of a 30:1 or greater (the etch ratio being the etch rate of material being etched versus the etch rate of underlying material). If you have too low an etch rate ratio, e.g., 10:1 or lower, you are likely to penetrate into the substrate too deeply or may undercut the material in question. The controlled time approach of end point detection is particularly unsuitable for reactive ion etch systems since reactive ion etching combines the etching power of the kinetic energy of the ion beam and the chemical properties, i.e., since selectivity is a chemical mechanism, you may have an etchant which is quite selective chemically, but effectively etches the underlying layer at a rate comparable to the rate for the overlying layer due to the kinetic energy of the ion beam. As stated previously, with highly complex or multi-layered circuits or with particularly thin underlying layers such as gate oxides in MOS devices, it is desirable to conduct etching steps to a specified depth to within 1000 Å. An ability to terminate an etch step within such a short distance may not be achievable with any of these techniques.

It is therefore an object of the present invention to provide an end point detection method in which the current through the target is measured to detect changes indicative of transitions between dissimilar materials.

It is another object of the present invention to provide a method for determining the end point of a physical etching step that is particularly suitable for reactive ion etching.

It is a further object of the present invention to provide a method for end point detection which instantaneously signifies the penetration by an ion beam through an overlying layer to a base layer.

BRIEF DESCRIPTION OF THE DRAWINGS

For a more complete understanding of the end point detection method of the present invention reference may be had to accompanying figures which are incorporated herein by reference and in which:

FIG. 3 is a block diagram of the circuit for electrical detection of current through the target;

FIG. 4 is a circuit schematic of the differentiator of FIG. 3;

FIG. 5 is a circuit schematic of the time discriminator of FIG. 3;

SUMMARY OF THE INVENTION

Figure 1:
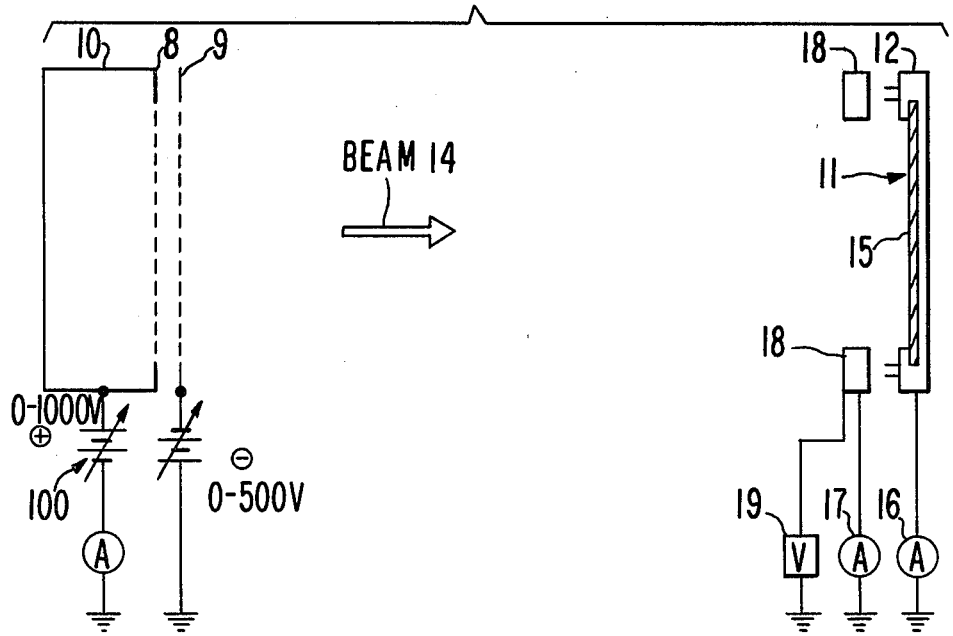
FIG. 1 is a pictorial diagram of an apparatus for practicing the method of the present invention.

End point is determined for a physical etching process step by measuring current through the target and by detecting changes in the measured current. Changes in this current are indicative of transitions between dissimilar materials or of depth of penetration in a particular material. Momentary changes in the etching flux, e.g., in an ion beam, may be factored out by measuring the current in a mask placed in the vicinity of the target and by subtracting mask current from current measured through the target.

DESCRIPTION OF THE PREFERRED EMBODIMENTS

Throughout this description the term "overlying layer" is used to describe the layer being etched, the term "base layer" is used to describe the layer next underneath the overlying layer, the terms "target" or "wafer" are used to describe the entity containing the overlying and base layers, and "end point" is used to signify the point in time at which some change is observed in the current measured through the target or wafer. The phrase "through the target" or "current through the wafer" is used in a general sense to include current measured at any point on the wafer; thus, it would include current measured on the back side of a wafer or current measured on the surface of the wafer around its periphery. Thus, both bulk resistance effects and surface layer resistance effects are covered by this term. Physically, the observed changes in current are believed to coincide with or be close in time to the point at which some portion of the overlying layer has been completely removed and the base layer partially exposed. It is this point at which the differential secondary electron or conductive effects in the base layer as compared to the effects in the overlying layer begins to be observable. From this point on, until all the overlying layer is completely removed, the predominant effect will continue to change the current measured through the target or wafer until the current characteristic of the base layer is observed. Since the end point is defined as the point at which the base layer begins to be exposed, the etching process must be continued for a time sufficient to completely expose the base layer. This continuation time is denoted as the overetch time and in the art is reckoned as a percentage of the time taken to etch through the overlying layer—the ion beam conditions and physical configuration remaining the same.

The mechanisms underlying the current measured through a target material undergoing ion bombardment are generally known. These include the effective resistance of the target and any holder which is an effect combining the resistance of all layers; the emission of secondary electrons from the surface layer being bombarded; the emission of secondary ions from the surface layer being bombarded; the trapping of charge in layers of semiconductor material; and tertiary effects whereby secondary electrons emitted from the substrate return to it (in some cases these charges may be deliberately introduced, e.g., by a neutralizer). These effects are dependent upon the material in question and directly affect current measured through a target being bombarded by an ion beam; they effectively contribute to or detract from real ion beam current. It should be recognized therefore that current measured through the target, described hereinafter as a semiconductor wafer, represents a combination of real ion current from the impinging beam and these other effects. These effects will depend upon the characteristics of the layer (overlying a base) exposed at any point in time and serve to permit one to infer which layer is in fact exposed. These effects permit a primary way of establishing end point which does not depend upon gross current levels but only on changes in the current.

Often, as in the ensuing description, the wafer is held in a platen so that measurements are most conveniently made at the platen. Thus, $$I_P = I_R - I_I + I_{SE}$$

where
$I_P$ = current from platen to ground
$I_R$ = real ions from impinging beam
$I_I$ = current due to secondary positive ions
$I_{SE}$ = current due to secondary electrons In a case where conductive mechanisms are not dominant $I_R$ can be considered constant or can be factored out by using a mask, as described subsequently to measure and subtract this term. In many cases the secondary emission of ions can be ignored. Thus, when secondary electron emission predominates:

$$dI_P = +dI_{SE}$$

and one may observe transitions between dissimilar materials since they will have differential electron emission characteristics. See G. Carter, et al., *Ion Bombardent in Solids*, Chp. 3, "Secondary Electrom Emission" (1968); D. E. Gray, ed., *American Institute of Physics Handbook*, "Secondary Emission," pp. 9-183 et seq., 3rd Edition (1972). It should be realized that $I_{SE}$ can be controlled by the bias voltage on a mask overlying the wafer/platen so this term can be increased or decreased at will. A positive bias will draw additional electrons from the surface and a negative bias will quench emission or repel emitted electrons and send them back to the substrate as tertiaries.

When conductive effects predominate, i.e., when secondary electron characteristics are similar, but the resistivities are different then $I_{SE}$ can be considered to be constant or small and:

$$dI_P = -dI_R$$

Thus, this term will decrease when one etches through a conductive overlayer to an insulating base layer and will increase when one etches through an insulating layer to a conductive layer. The former effect will produce a current curve that may be used to determine depth of penetration in an overlying conductive layer.

In most combinations of overlying and base layers the predominant effect can be predicted and/or empirically established. The remainder of the effects may be present but will be overshadowed by the observable predominant effect. It is the predictable predominance of a particular effect that permits the method of the present invention to determine the transition between different materials and, in certain cases, to determine depth of penetration in a given material.

An apparatus for practicing the method of the present invention will have the configuration shown pictorially in FIG. 1. This configuration is of the type exemplified by the RE-580 Reactive Ion Beam Etcher of Varian-/Extrion. It incorporates a wafer loading and unloading mechanism in accordance with U.S. Pat. No. 3,901,183 and is illustrative of the many configurations with which the method of the present invention may be practiced. An ion source 10 produces an ionic species or group of species which are extracted and accelerated down a linear path towards wafer 11 on platen 12 by means of voltages on extraction plates 8 and acceleration plates 9. Typically, the ion beam is unanalyzed so a broad beam Kaufman-type source may be used (e.g., the 15 cm) Kaufmann source of Ion Tech., Fort Collins, Colo.); this type of beam also permits greater area coverage with less complex equipment. Such broad beam sources are also rendered more usable due to the reliability and precision of the end point detection scheme of the present invention, i.e., greater non-uniformity can be tolerated in the ion beam for equivalent etch tolerances if it is known directly and with great precision when materials transitions occur.

The ion beam 14 will impinge upon semiconductor wafer 11 having an exposed surface 15. Typically, the exposed surface 15 will have a pattern defined by photoresist. The exposed surface areas will be etched at a rate dependent upon the constituent species of the beam, the beam energy, the characteristics of the material of the exposed layer including its chemical reactivity with the ionic species and its density or crystal structure. The material defined by the pattern and intended to be etched will typically be etched much faster than the photoresist. In any event, the thickness of the photoresist can be selected to be great enough to provide a significant margin of safety so that all exposed material is etched before the photoresist is depleted.

Figure 2:
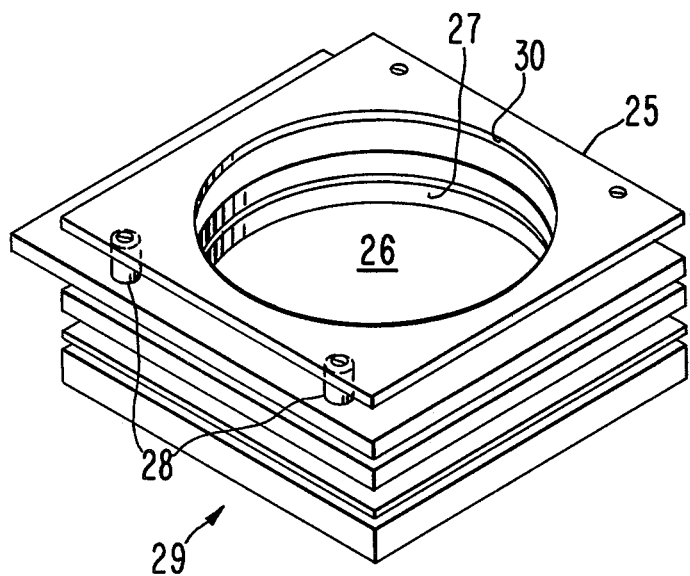
FIG. 2 is a perspective view of a platen and mask used in the apparatus of FIG. 1.

In accordance with the present invention, the semiconductor wafer 11 is mounted on and makes conductive contact with platen 12. The platen is preferably of the type that also makes good thermal as well as electrical contact with the wafer so that a conductive path exists from platen 12, through the back side, through the internal regions of the wafer up to the base layer and through the overlying layer. Alternatively, as with the Waycool TM platen disclosed in copending application Ser. No. 21,362 filed Mar. 15, 1979, and shown generally in FIG. 2, the semiconductor wafer is held by clamping ring 27 against a platen 26 coated with a pliable thermally conductive material. Since the pliable thermally conductive material is not a good electrical conductor the primary electrical contact is with the clamp on the surface of the wafer around its periphery. Thus, electrical current measured on the platen represents current that diffuses across the surface of the overlying layer to the clamping ring. As shown in FIG. 1, a current measuring circuit 16 is connected to the platen to measure current through the wafer (see earlier definition of this term). In a preferred embodiment the current through a conductive mask 18 is also measured by an ammeter 17 so that the instantaneous level of ion beam current can be factored out of the current measured through the wafer. This is shown in FIG. 2 as mask 25 separated by insulating spacers 28 from Waycool TM platen 29.

As described above, in a preferred embodiment the current through a mask adjacent the platen is measured in order to factor out momentary fluctuations in ion beam intensity. FIG. 3 is a block diagram setting out one way in which the mask and platen current signals may be processed. It involves early digitization and differentiation of the measured signals and is only one of many ways to process the current signals to detect changes. The current through the mask is introduced on line 31 as a reference current to a differentiator 33 (for detail see FIG. 4, described subsequently). The current through the wafer and platen is introduced on line 32 to differentiator 34. In each case the differentiator senses changes in the current whose derivatives have the same sign as the expected end point (since the predominant mechanism will be known in a given case the direction of the change in current will be known). The digitized outputs of the differentiators 33 and 34 are fed to a time discriminator 35 (for detail see FIG. 5, described subsequently) where the mask/reference current is effectively subtracted out and the duration of any real changes in platen current are compared against a time standard. When a deviation from a baseline current endures for a period longer than the time standard then it is deemed that an end point has occurred and the time discriminator sends a sharp output to the control logic 36 (for detail see FIG. 6, described subsequently). The series of curves on FIG. 3 illustrates that perturbation 37 in the platen current and 37' in the reference current are likely to be caused by fluctuations in the source and not by changes in the wafer; thus, no end point is signalled. Later when platen current begins to rise at location 38 an end point is signalled because the change occurs only in the platen and must be due to underlying physical changes in the wafer.

A differentiator suitable for use in the circuit for practicing the method of the present invention is shown in FIG. 4. The input current is introduced on line 43 to a three stage operational amplifier linear network. The operational amplifiers 40, 41 and 42 are National Semiconductor LM 351s and the transistor 46 is a 2M3904. Switch 44 renders the first stage a sign changer if it is thrown; this position would be used, for example, if it were known that the current through the platen were going to decrease rather than increase at end point. Thus, the rest of the circuit will only have to interpret positive going end points. The reverse logic pertains if it were known that the current through the platen were going to increase at end point. The second stage incorporates operational amplifier 41 and with appropriate values for the input and feedback capacitors and resistors differentiates the current signal. A second differentiation is accomplished by operational amplifier 42 to increase sensitivity. Then the output is isolated and taken from collector 45 of transistor 46. It is clear that the differentiators 34 and 35 of FIG. 3 would necessarily be functionally identical, i.e., would both be fabricated in accordance with FIG. 4 or some other circuit embodiment in order to permit tracking.

FIG. 5 illustrates an embodiment of a time discriminator of the type used in the circuit of FIG. 3. Circuit elements 50, 51, 52 and 57 are NAND gates such as those included in National Semiconductor 74C00. Circuit elements 53, 54, 55 and 56 are monstable/abstable multivibrators such as National Semiconductor CMOS 4047s. The platen current signal, e.g., the twice differentiated signal of FIG. 4, is introduced on line 58 to monstable/astable multivibrator 55. The reference signal is introduced on line 59 to monostable/astable multivibrator 55. The reference signal is introduced on line 59 to monostable/astable multivibrator 53. If a perturbation is experienced by both the mask and the platen, then the digital pulses from monostable/astable multivibrators 54 and 56 will have the opposite sign and NAND gate 57 will have no output. On the other hand, if the platen current signal on line 58 changes but not the mask/reference current signal on line 59 and this unmatched change continues for a period greater than the delay built into the monostable/astable multivibrators, then NAND gate 57 produces an output which triggers the latch formed by cross coupled NAND gates 50 and 51. The output of NAND gate 50 signifies the state of the latch and is taken at terminal 61 as the output of the time discriminator. After being triggered and thereby signalling detection of end point, the latch is reset on line 60.

Figure 6:
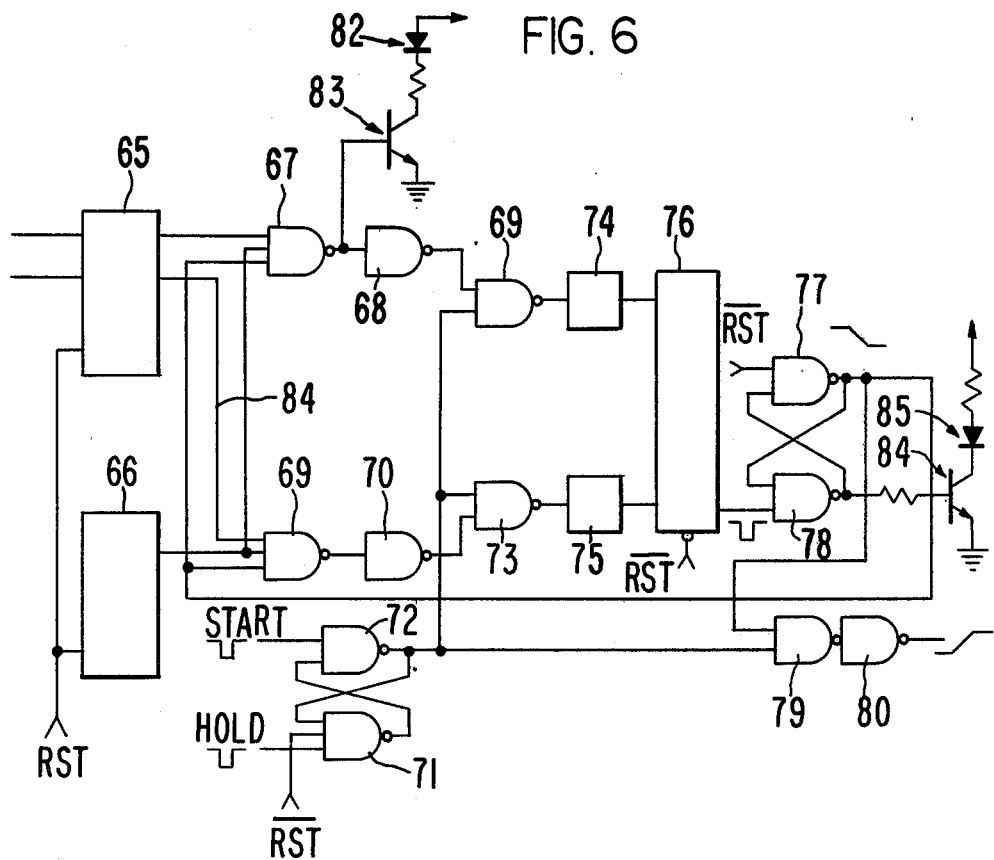
FIG. 6 is a circuit schematic of the control logic of FIG. 3.

FIG. 6 illustrates the control logic of the circuit of FIG. 3. The control logic serves to receive from time discriminator 35 an indication that end point has been reached. The control logic then directs the continuation of the etch for the overetch time which, as described above, is a predetermined fraction of the time to etch the overlying layer. The start of the etching of the overlying layer is signalled through NAND gate 72 to NAND gate 73 which starts clock 75 to oscillate to thereby produce an upward count in Counter 76; this counter may be fabricated from National CMOS 74C193 parts. This count continues throughout the etching period prior to end point. It may be placed on hold by the initiation of NAND gate 71 or, if the run is aborted, the counter 76 may be reset. Otherwise the count at the time end point is reached will represent the total etch time. When end point is signaled from the time discriminator 65, the output of NAND gate 67 is changed. At this end point the base on transistor 83 goes high and current is drawn through LED 82 which visually signifies end point. At the same time output 84 from time discrimanator 65 shifts thereby turning NAND gate 69 off so that through NAND gate 70 the NAND gate 73 is turned off and the up clock 75 is deactivated. Also at this time the NAND gate 69 shifts its state due to the signal from NAND gate 68; this in turn activates down clock 74 which begins a downward count in counter 76. The rate of clock 74 as compared to clock 75 will determine the extent of overetch. This relative rate is variable and can be controlled externally by an operator, typically in an overetch range of from 1 to 100%. When counter 76 reaches zero, a pulse is transmitted to NAND gate 78 which is cross connected with NAND gate 77 to form a latch. The output of NAND gate 78 turns transistor 84 on so that current is drawn through LED 85 which visually signifies end of overetch. Simultaneously, the output of NAND gate 77 turns NAND gate 79 on so that the output of NOR gate 80 can turn off or gate the ion beam source. At this point an automatic reset signal is introduced where indicated and the control logic is ready to control a new process step after receipt of a new start signal at the input of NAND gate 72.

As described subsequently minor changes in current measured through the wafer can definitively indicate a transition between materials. And for certain materials systems the increase or decrease in ion beam current can be used quantitatively to determine depth of penetration. Or the slope of the measured current can signify end points as with dual layer dielectrics where the change from one slope to another can signify that transition from one material to the other. In most cases it is desirable to factor out changes in ion beam current which are due to changes in intensity of the source. Therefore, in certain embodiments of the present invention a mask 18 is placed between the source 10 and the platen 12. The mask serves both to protect the platen from excessive build-up of ion beam residue and as a platform for receiving ion beam current which will be close on an area basis to that measured through the wafer. This mask may also be biased, as discussed subsequently.

The practice of the end point detection technique of the present invention is illustrated with particular materials combinations. The combinations shown are some of the major ones although many others are possible, including dual layer insulator silicon nitride on silicon dioxide, silicon nitride on III-V compounds, and semiconductors or metals. The following illustrative combinations also show the impact of the mechanisms, particularly the conductive and secondary electron emission mechanisms which have been described in general, previously.

CONDUCTOR ON INSULATOR

A final level on most integrated circuits would include metallization. This metallization must selectively interconnect portions of the integrated circuit and typically overlies an insulating layer of silicon dioxide or silicon nitride with contact being made with active regions through openings in the insulator. The definition of the interconnection pattern is accomplished by applying a patterned layer of photoresist over a sheet of the metallization material, e.g., over AlCuSi. The pattern is then fabricated by etching through the areas not covered by photoresist. For reactive ion etch materials such as the various chlorine species produced the disassociation of $CCL_4$ it has been found that effective etch rates of the substrate are greater than that of the photoresist. Also, the thickness of photoresist layer can be made to greater than that of the metallization so with any given etch step the metallization pattern is completely fabricated, i.e., the end point of the etch is reached and adequate overetching is obtained, before the photoresist is completely removed. As set out in general previously, the etching of the metallization can produce a current through the wafer and, as measured at the platen, which either increases (secondary electron emission predominates) or decreases (conducivity predominates). Examples of each are given:

EXAMPLE 1

Figure 7A:
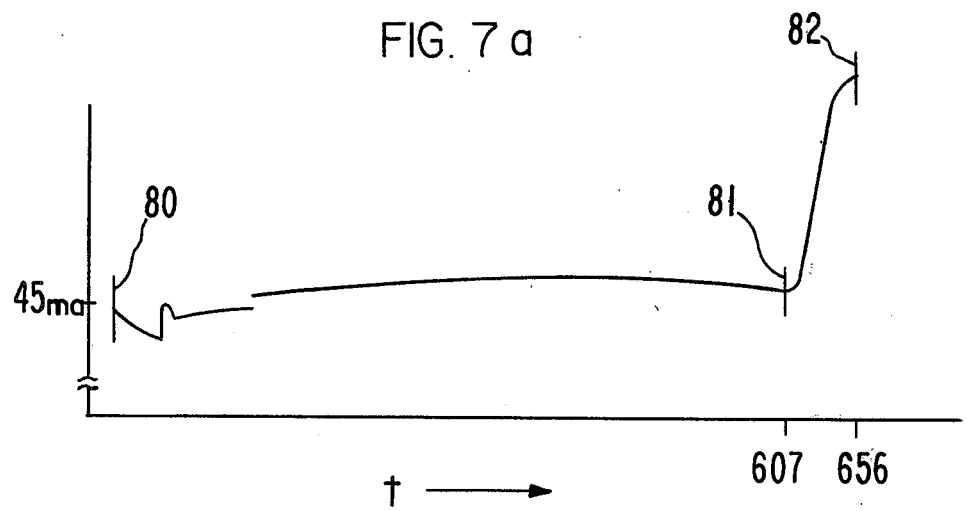
FIGS. 7a–7d are a series of profiles of ion beam current through the wafer versus time for different materials combinations.

As shown in FIG. 7a a semiconductor wafer having a photoresist defined pattern on an overlying layer of AlCuSi and a base layer of $SiO_2$ was etched in an ion beam current of 45 milliamps. The photoresist was Shipley AZ1350J of 1.5 $\mu$m thickness. The AlCuSi was 0.75 $\mu$m thick. The source was an Ion Tech Kaufmann 15 cm source in which $CCl_4$ was decomposed. The extraction voltage on plate 8 was 700 volts and the etch time to end point, vertical line 81 was 607.7 seconds. The overetch time, the time between line 81 and line 82, was 48.5 seconds and constituted in 8% overetch. No bias was applied to mask 18 so it is believed that the differential secondary electron mechanism was predominant.

EXAMPLE 2

Figure 7B:
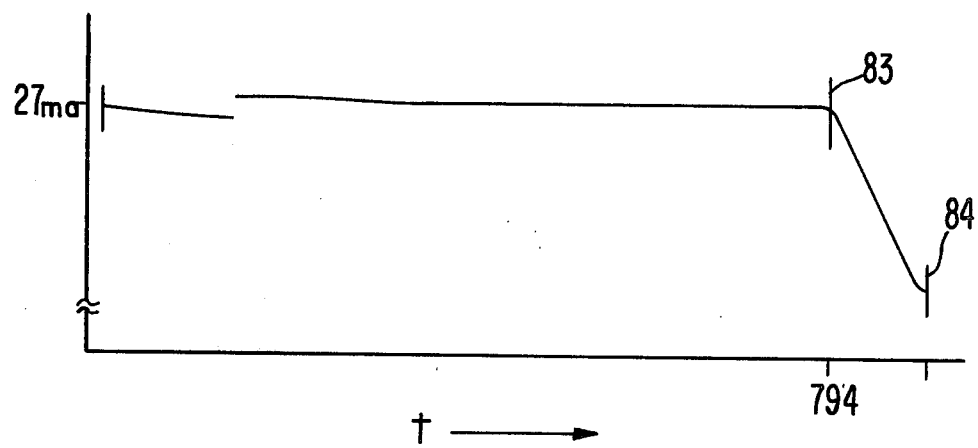

As shown in FIG. 7b a semiconductor wafer having a photoresist defined pattern covering a layer of AlCuSi was etched with a beam of the ionic constituents from the decomposition of $CCl_4$. The beam energy was 27 ma. The photoresist was 1.5 $\mu$m thick and the AlCuSi was 0.75 $\mu$m thick. The extraction voltage was about 675 volts. The time to end point was 794 sec and the overetch time was about 80 seconds. A 2.5 inch mask on a large wafer was used. In this case the apparatus of FIG. 1 was modified to include a bias ring about 10" downstream from the acceleration electrode 9 (about 15" from the wafer); no bias mask was used adjacent the wafer. The bias ring had a suppression voltage of −500 V applied to it and was protected on the upstream side by a gounded graphite mask. This reduced secondary emission and increased tertiary electrons returning to the wafer. Therefore, because of the effective negative bias the primary mechanism was conductivity, i.e., the resistance increased as the conductor layer was etched away and the current through the wafer decreased.

INSULATING LAYER ON SEMICONDUCTOR

Figure 7C:
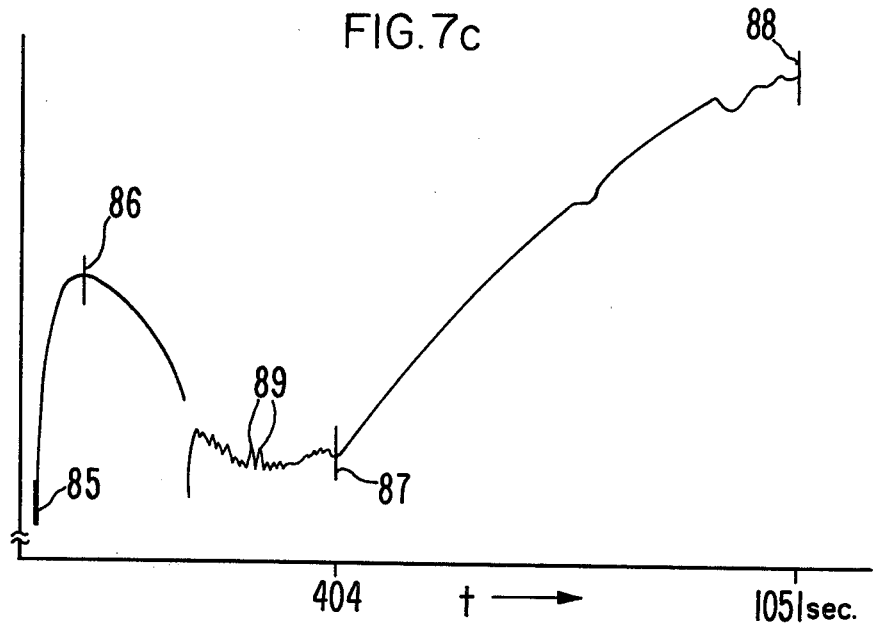

Intermediate levels in integrated circuits often include insulating layers such as layers of thermally grown silicon dioxide on crystalline silicon. Access to regions of the semiconductor silicon substrate is required for reach through of the metallization as discussed in the previous section. Therefore, etching of the silicon dioxide is required and is accomplished in accordance with the present invention by a physical etching process. In order to protect active device regions such as sources, drains or emitters the method for determining end point of the present invention is particularly applicable. In the example of FIG. 7c a 5000 Å overlying layer of $SiO_2$ on a silicon base was etched. As with the previous example a modified version of the apparatus of FIG. 1 was used in which a bias ring having a negative 500 volt bias was inserted about 9" downstream from the acceleration electrode. The bias ring was protected by a gounded graphite mask and no bias was applied to mask 18. The total time to completely remove the layer was 1051 sec. This was determined to be the point at which the current curve reached a plateau. A bias voltage of 500 was applied to the mask. The early rise in current from line 85 to line 86 is believed to constitute a breaking up of the $SiO_2$ into an amorphous mixture; at the peak the thickness was determined to be 6500 Å probably due to the incorporation of ion beam components into the mixture. At line 86 etching started to occur and down to line 87 the overlayer was diminishing in thickness. The current spikes 89 are believed, in fact, to be shorts of the ion beam through the amorphous mixture. At line 87 at about 404 seconds it is believed that some significant area of the silicon base is now exposed and current gradually rises due to the increase in conductivity through the $SiO_2$ to the Si.

POLYSILICONE ON SILICON DIOXIDE

Figure 7D:
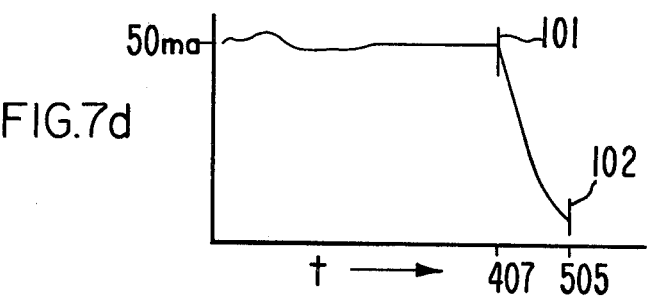

Polycrystalline silicon where heavily doped is used as a conductor in some MOS processes. Thus, it is patterned and etched for the reasons given above for overlying conductive layers. The apparatus of FIG. 1 was used to etch a 5000 Å sheet of overlying heavily n-type doped polysilicon on a base layer of silicon dioxide (5000 Å of silicon dioxide on single crystal silicon). A 15 cm Kaufmann source was used. The ion beam current at the wafer was 50 ma. The extraction voltage on plate 9 was 700 V. As shown in FIG. 7d, the time to end point, line 101 was 407 seconds and the total etch time was 505 seconds for an overetch of 19.4%. The primary mechanism is believed to be conductive as the resistance increased due to the elimination of the highly conductive overlayer.

While the method of the present invention has been described in connection with specific circuitry and specific materials combinations, it will be understood that it is capable of many modifications, and this application is intended to cover any variations, uses or adaptations of the invention following, in general, the principles of the invention, e.g., the measurement of current through the target and the detection of changes therein to determine end point. Thus, this application would cover departures from the present disclosure in the area of system configuration, bias levels, etc., and any other departures as come within known or customary practice in the end point detection art and as may be applied to the essential features hereinbefore set forth, and as fall within the scope of the invention and the limits of the appended claims.

We claim:

1. A method for determining the end point of a physical etching process step, comprising the steps of:
   measuring the current through a semiconductor layer having at least one overlying layer thereon being etched;
   measuring the current through a mask positioned in the vicinity of said layer;
   subtracting said current through said mask from said current measured through said semiconductor layer to produce a layer-dependent current component; and
   detecting changes in said layer-dependent current component as the physical etching step progresses with end point being indicated by detection of a change greater than a preselected amount.

2. A method for determining the end point of a physical etching process step as in claim 1 wherein said step of detecting changes in said layer-dependent current component is accomplished by the step of detecting the changes in the slope of said layer-dependent current component.

3. A method for determining the end point of a physical etching process step as in claim 1 in combination with the additional step of applying a bias voltage to said mask.

4. A method for determining the end point of a physical etching process step as in claim 1 wherein said step of measuring a current through a semiconductor layer is accomplished by the step of measuring a current through a semiconductor layer having two successive overlying layers of dissimilar materials.

5. A method for determining the end point of a physical etching process step in accordance with claim 4 wherein said step of measuring current is accomplished by the step of measuring current through a semiconductor layer having overlying layers of a conductive material on a base layer of an insulating material.

6. A method for determining the end point of a physical etching process step in accordance with claim 4 wherein said step of measuring current is accomplished by the step of measuring current through a semiconductor layer having overlying layer of silicon dioxide on a base layers of a semiconductor material.

7. A method for determining the end point of a physical etching process step in accordance with claim 4 in combination with the step of terminating the etching process after a given overetch time period.

* * * * *